(12) United States Patent
Biava (10) Patent No.: US 9,750,773 B2
(45) Date of Patent: Sep. 5, 2017

(54) FACTORS EXTRACTED FROM FISH EMBRYOS AND USE OF MIXTURES THEREOF IN THE CONTROL OF STEM CELL MULTIPLICATION AND DIFFERENTIATION

(71) Applicants: Michele Biava, Milan (IT); Maura Biava, Amsterdam (NL); Annamaria Ricotti, Milan (IT)

(72) Inventor: Piermario Biava, Milan (IT)

(*) Notice: Subject to any disclaimer, the term of this patent is extended or adjusted under 35 U.S.C. 154(b) by 0 days.

(21) Appl. No.: 14/818,819

(22) Filed: Aug. 5, 2015

(65) Prior Publication Data

US 2016/0038546 A1     Feb. 11, 2016

(30) Foreign Application Priority Data

Aug. 7, 2014    (IT) ........................ MI2014A001464

(51) Int. Cl.
*A61K 35/60*     (2006.01)
*A61K 8/98*     (2006.01)
*A61Q 19/08*     (2006.01)

(52) U.S. Cl.
CPC .............. *A61K 35/60* (2013.01); *A61K 8/987* (2013.01); *A61Q 19/08* (2013.01); A61K 2800/10 (2013.01)

(58) Field of Classification Search
CPC ..................................................... A61K 35/60
See application file for complete search history.

(56) References Cited

PUBLICATIONS

Ivanenkov et al. FEBS Letters, 1994, 352:227-230.*
Na et al. Cancer Sci., 2009, 100(8):1429-1433.*

* cited by examiner

*Primary Examiner* — Bin Shen
(74) *Attorney, Agent, or Firm* — Abelman, Frayne & Schwab (57) ABSTRACT

A cell growth and/or differentiation factor extracted from fish embryos in selected stages of stem cell differentiation, said stages being the mid-blastula-gastrula, tail bud and pharyngula stages. The invention also provides the use of growth and differentiation factors extracted from fish embryos in the control of stem cell multiplication and differentiation.

10 Claims, 8 Drawing Sheets

Analysis of zebrafish extract proteins:
5 stages of development (ZF1-ZF5) and a mix of the 5 stages (ZF6)

SDS page of the Embryonic Zebrafish extracts

FACTORS EXTRACTED FROM FISH EMBRYOS AND USE OF MIXTURES THEREOF IN THE CONTROL OF STEM CELL MULTIPLICATION AND DIFFERENTIATION

RELATED APPLICATIONS

This application claims priority from Italian Patent Application No. MI2014A001464 filed Aug. 7, 2014, incorporated by reference in its entirety.

FIELD OF THE INVENTION

The present invention concerns extracts from fish embryos and using mixtures thereof in the control of stem cell multiplication and differentiation.

The present invention originates in the epigenetic field and its applications in a nutritional, cosmetic and medical context.

Specifically, the present invention relates to cell growth and differentiation factors collected from fish embryo at specific stages of stem cell differentiation.

BACKGROUND OF THE INVENTION

The considerable increase in average age exposes ever-increasing segments of the population to the risks of developing tumours and chronic degenerative diseases. These conditions constitute one of the most serious health problems for which an effective therapeutic response is not yet currently available, due to the multifactorial causation and the complexity of the pathogenetic mechanisms involved in their genesis and development.

Some progress has been made in recent times as a result of stem cell biology studies, from which it emerges that tumour malignancy could be, at least in part, attributable to the presence of altered stem cells (cancer stem-like cells). This finding has directed numerous lines of research on the reprogramming of cancer stem-like cells.

The use of certain growth factors in the cancer stem-like cell reprogramming field and stem cell transplant research has led to the hypothesis that stem cell growth and differentiation factors could also be useful for determining the fate of normal, as well as altered stem cells, regenerating and/or differentiating them.

The present invention originates precisely in this field of scientific research.

A general aim of the present invention is to identify and provide cell growth and differentiation factors that play a key role in stem cell regulation and differentiation and to find an application for these factors in the nutritional and/or medical context. Another aim of the invention is to identify and select biological factors that are produced by the stem cells of fish species in specific stages of embryonic development and to find specific applications in the medicinal context, in particular, in the prevention and/or treatment of neurodegenerative diseases and/or tumoural forms.

SUMMARY OF THE INVENTION

The present invention originates in having identified specific differentiation stages of the stem cells of an embryo in which specific stem cell growth and/or differentiation factors are produced, which find application in the medical, nutritional or cosmetics field.

According to certain aspects of the invention, an innovative method is provided for directing the fate of normal or pathological stem cells.

The present description also contains teachings aimed at improving the efficiency and the therapeutic results achieved with stem cell transplantation and identifies alternative routes to transplantation itself.

According to some aspects, the invention originates from having found that the biological and therapeutic effects consequent to stem cell transplantation are not so much attributable to transplantation of the stem cells themselves but to stem cell production of cell growth and/or differentiation factors.

The applicant has now identified specific cell growth and differentiation factors and the properties that make them applicable in slowing down cell and normal aging processes and in treating certain conditions such as neurodegenerative diseases and tumours.

It has, in particular, been found that a mixture of the cell growth and differentiation factors of selected stages have an effective cell regeneration and therefore find application in slowing down the body's aging process and have an anti-aging action. The factors extracted in three selected stages can then be combined with other factors extracted from further specific stages of stem cell differentiation, expanding the envisaged possibilities of use in the medical, nutritional, and cosmetic field for the factors extracted in the two selected stages of differentiation. According to a first aspect of the present invention, extracts of embryo stem cells, typically of fish, comprising three selected stages of embryonic stem cell differentiation or of embryonic development, are therefore provided, said stages being the mid-blastula-gastrula, tail bud and pharyngula stages.

It was found that mixtures of cell growth and/or differentiation factors extracted in selected stages of embryonic development, in particular of fish, play a part in the stem cell regeneration process and therefore find application in all the processes in which cell repair action and tissue regeneration is required, such as for example in the case of burns, necrotic tissue processes, in particular, of the epidermis, in fistulae, pressure sores or as antiaging agents for example.

In the course of experimenting on the stem cells of fish species, it was also observed that growth and/or differentiation factors extracted in the differentiation stage of the embryonic stem cells at/or 24 hours after fertilisation intervene and exert an influence in the cell differentiation stage.

The applicant has thus surprisingly found, according to a second aspect of the invention, that combining extracts from embryo stem cells in said mid-blastula-gastrula, tail bud stages with extracts from embryo stem cells in one phase of the pharyngula stage, in particular an early phase of pharyngula, achieves a combined stem cell regeneration and differentiation action.

In particular, the combination or mixture of cell growth and/or differentiation factors according to this second aspect of the invention finds application in regulating the cell processes that are at the basis of aging and cell death. According to some embodiments, the combination of factors collected in these stages find application in preventing and/or treating degenerative diseases of the central nervous system, such as Alzheimer's or Parkinson's and/or of the cardio-circulatory system such as in the case of myocardial infarction.

The applicant has also found, according to a third aspect of the invention, that combining extracts or cell growth and/or differentiation factors extracted from embryo stem cells in the mid-blastula-gastrula stage and tail bud stage with cell growth and/or differentiation factors extracted in the 5-somite, 20-somite stages of differentiation and in the pharyngula differentiation stage, a particularly intense combined differentiation and cell regulation action is obtained.

This combined action finds application in the medical field typically in preventing and treating conditions associated with an increased cell replication rate, as in the case of tumours or diseases of the skin in which the epithelial cells have a greater cell replication rate than normal, as in the case of psoriasis, eczema, erythematosus lupus, atopy.

According to some embodiments of the invention, the growth and differentiation factors used in the context of the invention are obtained from stem cells from zebrafish.

According to a fourth aspect, the present invention provides a composition comprising cell growth and/or differentiation factors extracted from embryo stem cells according to one of the previously described aspects of the invention and an edible and/or pharmaceutically acceptable carrier.

According to some embodiments, the composition of the invention is a pharmaceutical composition in which the carrier is or comprises a pharmaceutically acceptable excipient.

According to other embodiments, the composition of the invention is a nutraceutical or dietetic product or a food for special purposes or a cosmetic composition.

BRIEF DESCRIPTION OF THE DRAWINGS

Some of the characteristics and advantages of the present invention will be apparent from the accompanying drawings, wherein.

DETAILED DESCRIPTION OF THE INVENTION

The applicant, studying the differentiation of embryonic stem cells of fish in particular, has identified stem cell growth and differentiation factors that are useful for regenerating and/or differentiating stem cells.

In particular, the invention originates from:
A) having identified the most significant moments of the differentiation of various types of stem cells,
B) having analysed and selected the two early stages of stem cell differentiation in which essential factors for cell regeneration are produced,
C) having identified the specific percentage distribution of the protein fractions present in the two selected stages and the proteins produced in those specific early stages of cell differentiation, in particular at the time in which the stem cells differentiate from totipotent to pluripotent;
D) having found specific applications in the medical field for the cell growth and differentiation factors identified by performing in vitro studies, for example by analysing the effects on the multiplication, proliferation, and differentiation of human mesenchymal stem cells collected from adipose tissue.

According to some aspects of the invention, it was thus found that by providing extracts from fish embryo, in particular containing stem cells in specific stages of embryonic development or stem cell differentiation, we are intervening in the regulation and/or differentiation of human cells.

This approach revolutionises the conventional approach of using stem cells to intervene in some cell mechanisms deemed at the origin of diseases that originate from an uncontrolled cell growth.

According to a first aspect of the present invention, an extract obtained by extraction from a fish embryo, in particular zebrafish, on the differentiation stage of embryonic mid-blastula-gastrula, tail bud, and pharyngula stem cells, is provided.

In certain embodiments, cell growth and/or differentiation factors extracted in the differentiation stage of embryonic mid-blastula-gastrula, tail bud and pharyngula stem cells are provided for use in preventing or treating cell aging and in general, human body anti-aging.

According to another aspect, the invention provides an extract from fish embryos, in particular zebrafish, in the pharyngula stage. According to certain embodiments i) the extracts or ii) cell growth and/or differentiation factors extracted from embryo stem cells in the mid-blastula-gastrula stage and in the tail bud and pharyngula stage have the following percentage distribution of protein fractions, referring to the total proteins having molecular weight of less than 100 Kdaltons protein fraction of 14 kilodaltons: 14.6%
protein fraction of 20 kilodaltons: 4.2%
protein fraction of 25-30 kilodaltons: 28.4%
protein fraction of 45 kilodaltons: 14.8%
protein fraction of 97 kilodaltons 38%.

According to certain embodiments of the invention, a mixture comprising extracts from fish embryos containing an amount ranging from 20 to 40% of extracts in the mid-blastula-gastrula stage and an amount from 20 to 40% of factors extracted in the tail bud stage and from 20 to 40% of extract from pharyngula.

In certain embodiments, the fractions of factors extracted from the pharyngula is in amount from 30 to 70% the remaining being extracts from mid-blastula-gastrula stage and from the tail bud stage.

The preparation of the growth factors or embryonic extracts that contain them can be achieved following conventional techniques. In certain embodiments, preparation of the growth factors or embryonic extracts of the invention comprises the following steps:

a) embryos are collected at a specific stage of embryonic development;
b) a solvent is added;
c) the mixture obtained in step b) is subjected to agitation, with a turbo-emulsifier for example;
d) the mixture is optionally filtered, by 90 micrometer filters for example and
e) with 5-10 micrometer filters for example.

A stock solution is obtained from step c), which can be diluted with one or more conventional biocompatible solvents to obtain solutions with different degree of dilution depending on needs and uses.

According to some embodiments, the solvent used in step b) is based on a mixture of glycerin and an aqueous solution of ethyl alcohol, for example 30% v/v, typically in a glycerol/alcohol ration of 85:15 v/v.

The weight ratio of said solvent and said embryos is preferably between 20:1 and 2:1.

The agitation of step c) is preferably carried out at room temperature, as also applies to the other operations, for a period of time typically ranging from 1 to 2 hours.

According to some embodiments, step c) of mixing or agitation is performed with a turbo-emulsifier, emulsifying each one 1 to three times for 1-4 minutes.

According to a second aspect, the present invention provides a mixture or combination of extracts or cell growth and/or differentiation factors extracted or collected from embryo stem cells in the differentiation stage of embryonic mid-blastula-gastrula stem cells and in the tail bud stage with factors selected in the early pharyngula differentiation stage.

This combination of factors exerts an effective regeneration and cell differentiation action on the stem cells and finds application in the medical field in preventing and treating conditions associated with an abnormal or accelerated cell replication rate. The applicant has also found that the combination of cell growth and/or differentiation factors extracted from embryo stem cells according to this latter aspect has a combined action on cell regeneration and differentiation that makes them suitable, in the medical field, in preventing and treating chronic degenerative diseases.

In certain embodiments, the mixture of cell growth and/or differentiation factors contains 25% by weight of factors extracted in the mid-blastula-gastrula stage, 25% of factors extracted in the tail bud stage and 50% of factors extracted in the pharyngula differentiation stage, in particular in the early pharyngula stage.

According to a further aspect of the present invention, a combination of cell growth and/or differentiation factors extracted from embryo stem cells in the mid-blastula-gastrula stage and tail bud stage with factors in the pharyngula differentiation stage, are therefore provided, for use in treating chronic and/or neurodegenerative diseases such as Alzheimer's, Parkinson's, cognitive decline or in the treatment of a cardiovascular or cardiodegenerative disease such as heart attack, for example.

According to another aspect, the present invention provides a mixture or combination of cell growth and/or differentiation factors extracted or collected from embryo stem cells in the differentiation stage of embryonic mid-blastula-gastrula stem cells and in the tail bud stage with factors in the differentiation stage selected in the 5-somite, 20-somite stages and in the pharyngula differentiation stage, in particular in the early pharyngula stage.

In certain embodiments, the mixture of extracts from fish embryos or cell growth and/or differentiation factors contains 5% by weight of factors extracted in the mid-blastula-gastrula stage, 10% of factors extracted in the tail bud stage, 10% of factors extracted in the 5-somite stage, 25% of factors extracted in the 20-somite stage, 50% of factors extracted in the pharyngula stage.

The mixture of factors according to this latter aspect of the invention finds application in the medical field in the treatment of conditions with abnormal cell replication rate as in the case of tumours or of certain affections of the skin such as in cases of psoriasis, eczema, erythematosus lupus, atopy.

The applicant has further, experimentally observed that the cell growth and differentiation factors, in particular in the mixtures of stages 1 and 2 with the 5-somite, 20-somite stages and in the pharyngula stage, determine a slowing down of cell proliferation and an increase in programmed cell death, or apoptosis, while the early stages have even highlighted a multiplicative effect.

None of the stages and doses tested lead to death by necrosis or to toxicity for the cells. The extracts have thus proved harmless, and safe.

The experiments carried out have also demonstrated that when the information is sufficiently complete, unexpected results are obtained, both in protection against the insults that cause degeneration and tissue damage. This fact was confirmed by the experiments that related to the proliferation or, on the contrary, slowdown of the multiplication of mesenchymal stem cells, which demonstrate that they can therefore be directed both toward regeneration and toward differentiation, through the specific and selective use of the various protein networks identified in the individual differentiation stages of the embryo, in particular of zebrafish, and above all, through the use of the mixtures thereof, or of the mixtures of multiple differentiation stages. The experimental data reported in the examples demonstrate that the various growth and differentiation factors studied have the ability to selectively and specifically regulate various genes that are the expression of cell staminality or differentiation.

Within the present description, the terminology extract(s) from fish embryo(s) substantially has the same meaning of cell growth and/or differentiation factors. Typically, the cell growth and/or differentiation factors mentioned in the present description are extracts from fish embryos.

The term factors should be intended as cell growth and/or differentiation factors. The growth and differentiation factors studied constitute are epigenetically able to regulate stem cell gene expression, so as to direct them toward regeneration and/or toward differentiation. This finding is very important in both regenerative medicine, where tissues are to be regenerated, such as in the case of ulcers, wounds, etc., or tissues are to be regenerated tissues in the case of degenerative diseases.

This data supports the use of the factors related to the invention in stem cells transplantations, considering that, being small molecules having a low molecular weight, as demonstrated by the proteomics studies reported herein, they have a sublingual or percutaneous absorption.

A randomised, controlled clinical study of 179 cases of intermediate, advanced stage hepatocellular carcinoma, in which other treatments were no longer possible and therefore compassionately treated with these factors, sublingually, demonstrated regression in 20% and non-progression in 16% with a significant increase in the survival of patients treated. There is therefore a percutaneous absorption of these factors in psoriatic patients, in whom the unilateral treatment of lesions has resulted in an improvement or a disappearance of even contralateral lesions.

The cell differentiation factors or extracts from fish embryo of the invention can consequently find application a) as anti-aging agents
b) as tissue regeneration factors to treat scars, pressure ulcers, varicose ulcers, etc.
c) in conjunction with stem cell transplantations to improve the clinical effect of the transplantations
d) for preventing or treating various chronic degenerative diseases, such as neurodegenerative diseases, for example Parkinson's, Alzheimer's, multiple sclerosis, ALS, cardiovascular diseases, for example ischaemic cardiopathy, myocardial infarction, stroke and tumour. The extract of the invention finds application in treating stroke (Therapeutic Effects of hMAPC and hMSC Transplantation after Stroke in Mice, 2012 Silvia Mora-Lee et al. in PLoS ONE 7(8): e43683. doi:10.1371/journal.pone.0043683 editor: Brahim Nait-Oumesmar, Université Pierre et Marie Curie-Paris6, INSERM, CNRS, France).
e) in ocular conditions related to aging, such as exudative maculopathy According to certain aspects, the invention relates to extracts or the factors and the mixtures thereof according to any one of the previously described embodiments and compositions that contain them, for use in combination with stem cell transplantation or to replace stem cell transplantation.

In according with certain aspects the invention provides the cosmetic use of an extract from a fish embryo which is extracted in stages of stem cell differentiation of the mid-blastula-gastrula, tail bud and pharyngula stages for treating wrinkles of the skin or skin aging.

According to certain aspects, the present invention therefore provides a composition comprising extracts or cell growth and/or differentiation factors extracted from embryo stem cells according to any one of the previously described aspects and embodiments.

According to some embodiments, the composition of the invention is a pharmaceutical composition, a dietary supplement or a nutraceutical that can be introduced into the dietary regiment of an individual suffering from one or more of the previously described affections or conditions.

In some embodiments, the composition of the invention is a nutraceutical product comprising the mixtures of factors according to the previously described embodiments and an edible carrier. The nutraceutical product of the invention finds use in improving the nutritional conditions of the human body or performance status and quality of life.

In some embodiments, the composition of the invention can further comprise active substances, vitamins, nutritional substances, micronutrients, and/or minerals.

The term "carrier" as used herein, indicates a medium, excipient, diluent with which the combination of therapeutic or active substances is administered.

Any carrier and/or excipient suitable for the form of preparation desired for administration to humans is contemplated for use with the compounds described in the present invention.

For the purposes of the present application, the term "physiologically acceptable" or "edible" indicate edible substances that are approved by the health authorities for use in pharmaceutical, nutritional or dietary applications.

A physiologically acceptable carrier can be a pharmaceutically acceptable carrier. The compositions of the present invention comprise any composition produced by administering the extract or cell growth and differentiation factors of the present invention and a physiologically or pharmaceutically acceptable carrier. These compositions are suitable for dietary, nutritional, pharmaceutical, or dietetic use in mammals, in particular in human beings.

According to some embodiments, the composition of the invention is a food for special medical purposes.

According to another aspect, the present invention relates to a therapeutic treatment method of a disease selected among degenerative disease, in particular neurodegenerative disease, cardiovascular or tumour disease, comprising the administration of a therapeutically effective amount of an extract from fish embryo in the mid-blastula-gastrula, tail bud and pharyngula, and optionally 5-somite and 20-somite stages of cell differentiation.

In accordance with an aspect the invention provides for a method for the prevention or treatment of a degenerative diseases of the human body comprising the administration of a therapeutically effective amount of an extract taken from a fish embryo, especially zebra fish, as defined above. In certain embodiments said degenerative diseases is a neurodegenerative or cardiovascular disease.

In accordance with another aspect the invention provides a method for the prevention or treatment of cancer comprising the administration of a therapeutically effective amount of an extract as defined above.

In accordance with a further aspect the invention provides a method for regenerating a human body tissue comprising the administration of a therapeutically, regenerative effective amount of an extract as defined above.

In a yet further embodiment the invention concerns a cosmetic method of treatment of the skin, skin aging especially, comprising the application of a cosmetically amount of an extract as defined in one of the above mentioned embodiments.

The composition of the invention can take a wide variety of preparation forms, depending on the desired route of administration.

For example, for oral administration, the composition can be in solid form, as tablet, capsule, powder, granular, prolonged-release formulations of the active substances, for example. The compositions in solid form, in particular in granular or powder form, are preferred with respect to the other types of preparations.

The preparations in solid form can comprise one or more carriers such as starches, sugars, microcrystalline cellulose, and optionally diluents, granulating agents, lubricants, binders, disintegration agents, for example.

The tablets, pills, capsules, granules can also contain a binder such as tragacanth, acacia, corn starch or gelatin; excipients such as dicalcium phosphate; a disintegrating agent such as corn starch, potato starch, alginic acid; a lubricant such as magnesium stearate; a sweetening agent such as sucrose, lactose or saccharin. If desired, the tablets can be coated by traditional techniques.

When the pharmaceutical form unit is a capsule, it can contain, in addition to the materials of the above-mentioned type, a liquid carrier such as an adipose oil.

In the case of preparations in liquid form for oral administration, such as for example in the case of suspensions, emulsions, solutions, a suitable carrier can be selected from water, glycols, oils, alcohol, and mixtures thereof.

Flavouring agents, preservatives, colouring agents and the like can also be present in the composition.

In some embodiments, the growth factors contained in the composition of the present invention can be combined or mixed as active substances in intimate mixture with a suitable edible carrier and/or excipient according to pharmaceutical and food industry or traditional nutritional techniques.

The compositions for pharmaceutical, cosmetic or nutritional use can be adequately presented in single pharmaceutical form and prepared by any well-known technique of the pharmaceutical or dietary art.

In some embodiments, the compositions or preparations of the invention can contain at least 0.0001% of each growth factor. The amount of growth factors present in these compositions is such that a prophylactically or therapeutically effective dosage will be obtained.

In some embodiments, the composition of the invention further comprises one or more additional components such as additives, fillers, stabilisers, emulsifiers, texturisers, film-forming agents, plasticisers, humectants and thickeners.

Various other materials can be present, such as coatings or to modify the physical form of the pharmaceutical unit. For example, tablets can be coated with shellac, sugar or both. To prevent disaggregation during transit through the upper part of the gastrointestinal tract, the composition can be a formulation with enteric coating.

A syrup or elixir can contain, in addition to the active substance, sucrose as a sweetening agent, suitable preservatives, a colourant and a flavouring agent such as cherry or orange flavour.

In some embodiments, the composition of the invention is a cosmetic composition comprising a cosmetically acceptable carrier.

Suitable cosmetic compositions are in the form of a cream, lotion, serum or emulsions of the oil/water type.

The cosmetic compositions of the invention find application in the treatment of skin aging, in the cosmetic treatment of wrinkles, skin blotches and dry and desquamating skin, for example.

According to certain embodiments, the pharmaceutical composition is for use in medicine in combination with stem cell transplantation or to replace stem cell transplantation.

In some embodiments, the formulation will contain quantities of growth factors that will depend on the severity of the associated symptoms, the condition, the further therapies underway, the individual's state of health and on the response to the combination of active substances. In some embodiments, the dose is in the range of 0.00001% to about 10%, of 0.0001 to 5% of 0.001 to 1%, of 0.10 to 1% by weight of the total weight of the composition.

The present invention will now be described below with reference to the following examples, which are provided for illustrative purposes only and are not to be construed as limiting the present invention.

EXAMPLES

Example 1

Effect of cell growth and differentiation factors extracted in the mid-blastula-gastrula, tail bud, 5-somite, 20-somite stages and in the pharyngula stage from zebrafish embryo taken individually and in mixtures, on the proliferation and differentiation of mesenchymal stem cells (hMSC).

Materials and Methods:
1. Cell model: adult human mesenchymal stem cells isolated from adipose tissue (hMSC) by means of the Lipogems system,
2. Determination of the protein concentration in the zebrafish (ZF) extracts and: assay with BCA,
3 Identification of the different individual proteins: Nano-LC-MS/MS (liquid chromatography combined with mass spectrometry) analysis
4 Study of cell proliferation: assay with MTT
5. Gene expression analysis: Relative quantitative RT-PCR 1. Adult Human Mesenchymal Stem Cells Isolated from Adipose Tissue (hMSC) by Means of Lipogems hMSC were isolated from human adipose tissue using Lipogems. This is a device for collecting stem cells from lipoaspirates using a mechanical approach instead of enzymatic digestion.

2. Assay with BCA (Protein Determination in the Extracts)

The protein content in the zebrafish extracts was determined using the BCA assay, which is a colorimetric assay for the quantification of protein. The protein content in each extract was assessed in quadruplicate using bovine serum albumin (BSA) as standard. The protein concentration in the extracts ranged from 1.5-2.7 mg/ml.

3. Nano-LC-MS/MS Analysis

The proteins were identified by means of LC-MS/MS analysis. The MS/MS analysis of peptides generated by in-gel digestion in gel was accomplished by a nano-LC-ESI-Q-TOF (QSTAR Elite, Applied Biosystem) apparatus. HPLC was accomplished on an LC Packings Ultimate 3000 nanoflow (Dionex, Sunnyvale, Calif.) system. Samples (5 µL) were injected into a C18, 5 µm, 100 A, 300 µm I.D.×5 mm (LC Packing, Dionex) cartridge trap at 30 µL/min for 5 min (2% ACN, 0.1% formic acid) to enrich and purify the peptides. The capillary separation of the peptides trapped was performed using a C18, 5 µm, 300 A, 75 µm I. D.×15 cm Vydac (Grace) column. The chromatographic conditions and mass parameters were adjusted as follows: buffer A (2% ACN, 0.1% formic acid) and buffer B (2% water, 0.1% formic acid in ACN) with the gradient of 8-50% buffer B in 35 min, 50-80% in 15 min, 80% for the next 15 min and 80-8% in 5 min, lastly the column was re-equilibrated at 8% B for 10 min. For each TOF MS (350-1300 m/z) scan, the two ions with more intense double or triple charge were selected for the ionic scans of the potential product (110-1600 m/z). The ion spray voltage was 1.6 kV, the gas barrier was set to 15 and the potential sputtering was 80V. Mascot V1.6b20 (Matrix Science, London) software was used for the protein database search. Searches were performed using the NCBI database and the following standard parameters: zebrafish; tryptic digest with at most a scission failure; carbamidomethylation of cysteine, partial oxidation of methionine, and a mass tolerance of 100 ppm. For MS/MS data, the searches were performed with the following additional criteria: maximum tolerance of 0.3 Da for MS/MS data and the search for 2+ and 3+ peptide charge.

Chemical Compounds and Reagents.

The general chemical compounds were obtained from Sigma-Aldrich (Poole, UK). All the chemical and biochemical compounds used were of analytical grade.

4. Assay with MTT (Cell Proliferation)

The proliferation of human mesenchymal stem cells after treatment with zebrafish extracts was determined using the assay with MTT. In metabolically active cells, MTT is converted into formazan, which can be spectrophotometrically evaluated. The amount of formazan is proportional to the number of cells in the well.

Optimisation

Initially, preliminary studies were performed to determine optimal cell density, as well as the time for the metabolism of MTT. The following experimental conditions were selected on the basis of these studies:

Number of cells: 4000 or 5000 seeded cells per cm$^2$ in a 48-well plate.

Treatment: The Cells were Treated with Extracts of Zebrafish in the Following Stages:
  stage 1: mid-blastula-gastrula stage
  stage 2: tail bud stage
  stage 3: 5-somite stage
  stage 4: 20-somite stage
  stage 5: early (typically around 24 hours after fertilisation) differentiation stage of the pharyngula stage
  stage 6: mixture of the stages 1-5;
  each stage at four different concentrations: 10, 1, 0.1, 0.01 µg/ml and incubated for 24 or 72 h respectively.

MTT metabolism time: 3 h

Statistics: The data is presented as mean absorbance compared with respect to the control (untreated cells).

Results

Figure 1:
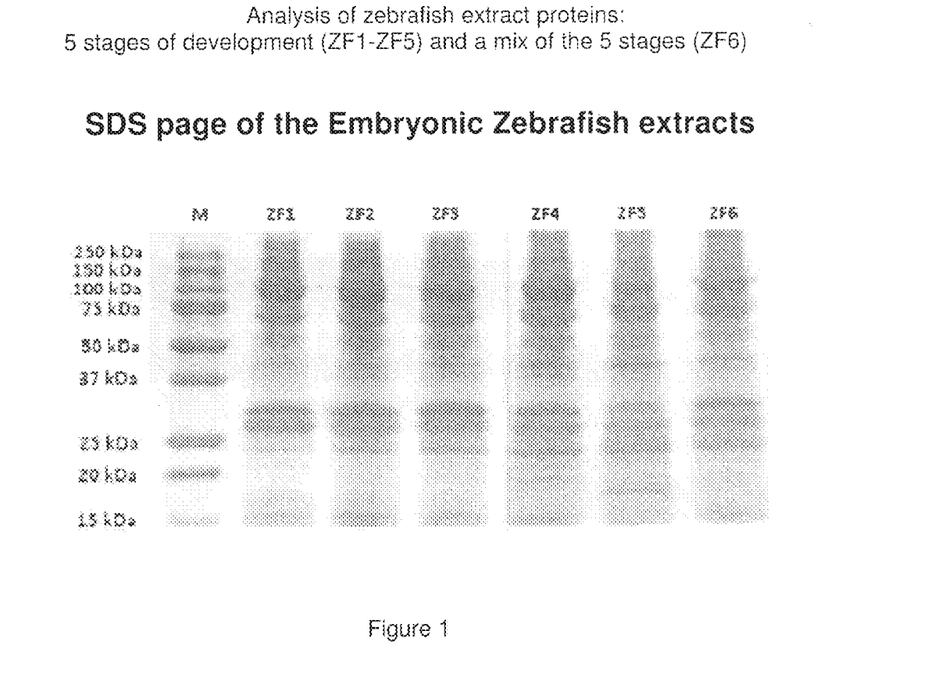
FIG. 1 illustrates analysis of the proteins of the factors extracted from the stem cells of zebrafish in 5 stages of development and the mixture of the 5 stages.

The results on the fractions having different molecular weight for the different stages of differentiation are indicated in FIG. 1.

Table 1 below, indicates the individual different proteins identified by LC-MS/Ms analysis.

Results of the Cell Proliferation Tests

Cell proliferation after 24 h and 72 h of incubation with zebrafish extracts, in different independent experiments.

The data is presented as normalised absorbance (treated cell abs/untreated cell abs) and as the average of 3 independent experiments.

Figure 2:
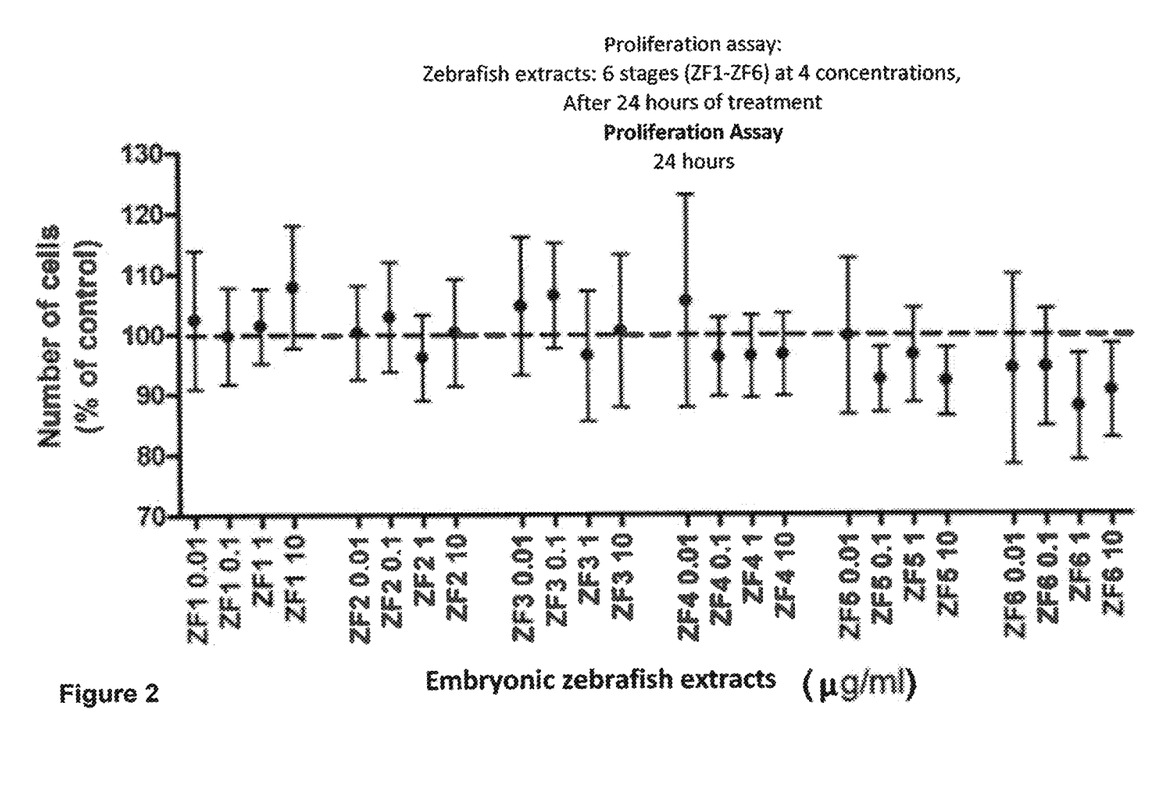
FIG. 2 illustrates a graph which reports the results of a proliferation assay (MTT) at 24 hours on human mesenchymal stem cells (hMSC) of individual growth factors (ZF1-ZF5) and of the mixture thereof (ZF6) at 4 concentrations.

The results of the assay with MTT after 24 h of treatment with zebrafish extract are illustrated in FIG. 2.

From the data, the following can be concluded:
  After 24 h of treatment, there was a slight reduction in proliferation;
  Extract 6 (mix of all the stages) had the most pronounced effect, and the effect was more evident with the minimal concentration (i.e. 0.01 µg/ml).

Figure 3:
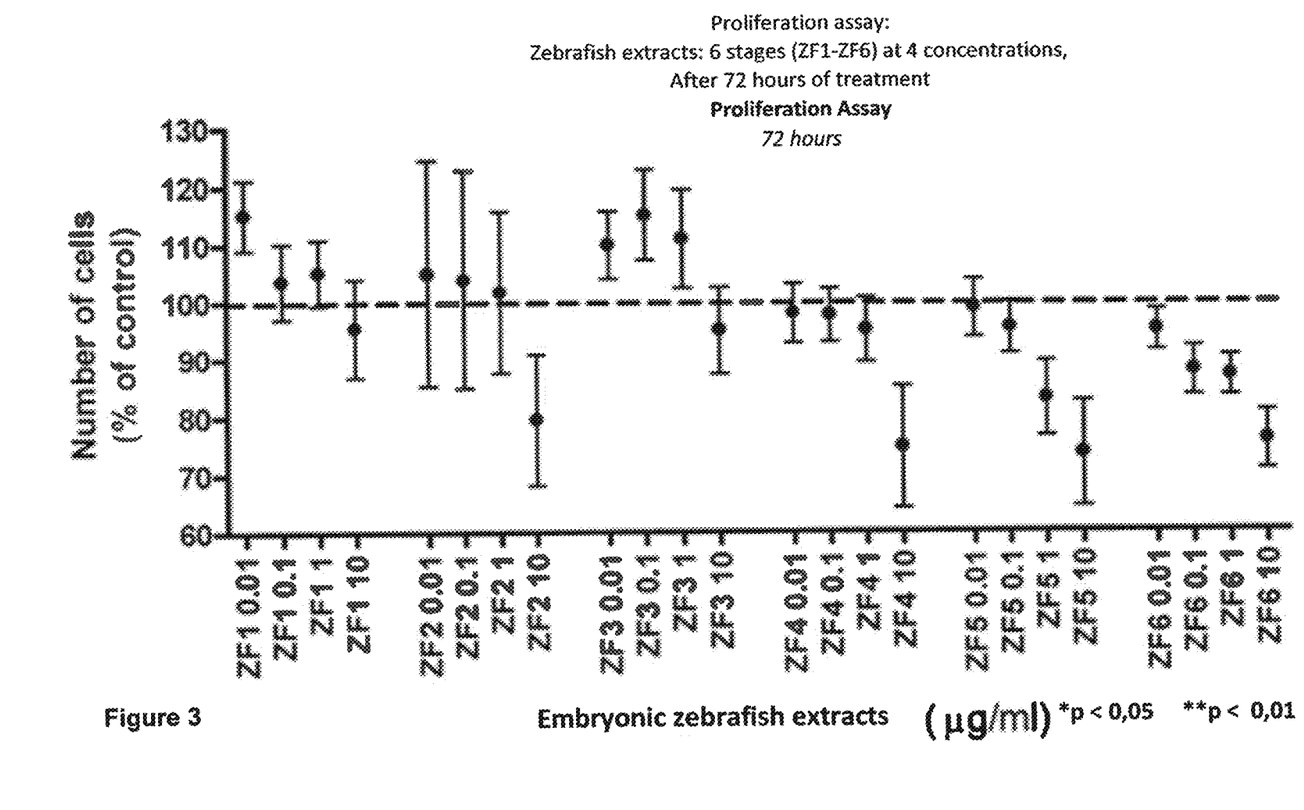
FIG. 3 shows a graph which reports the results of a proliferation assay (MTT) at 72 hours on human mesenchymal stem cells (hMSC) of individual growth factors (ZF1-ZF5) and of the mixture thereof (ZF6) at 4 concentrations.
Figure 4:
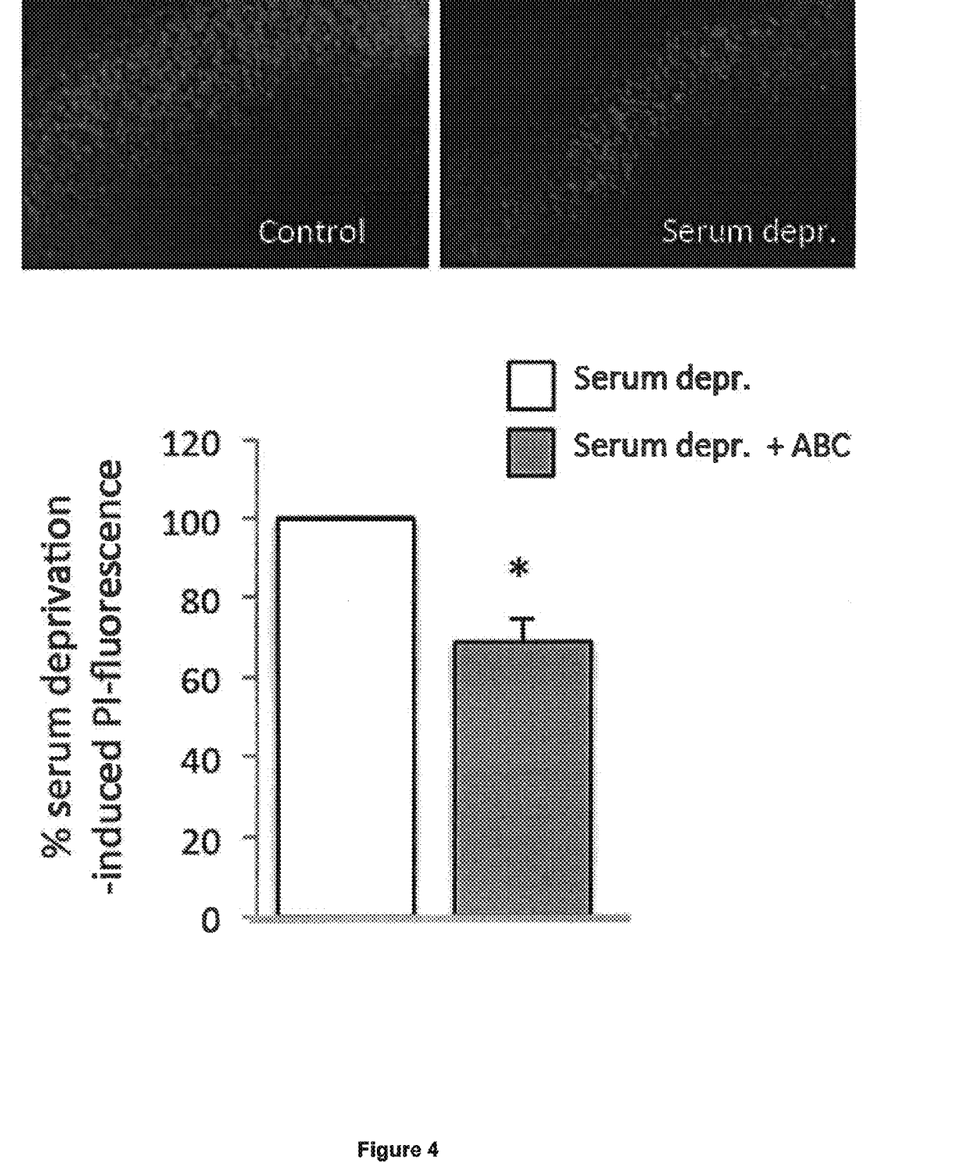
FIG. 4 shows bar graphs that illustrate the level of immunofluorescence with propidium iodide of the CA1 area of the hippocampus 24 h after 1 h of serum deprivation in the presence or absence of the ABC mixture of factors of example 2.
Figure 5:
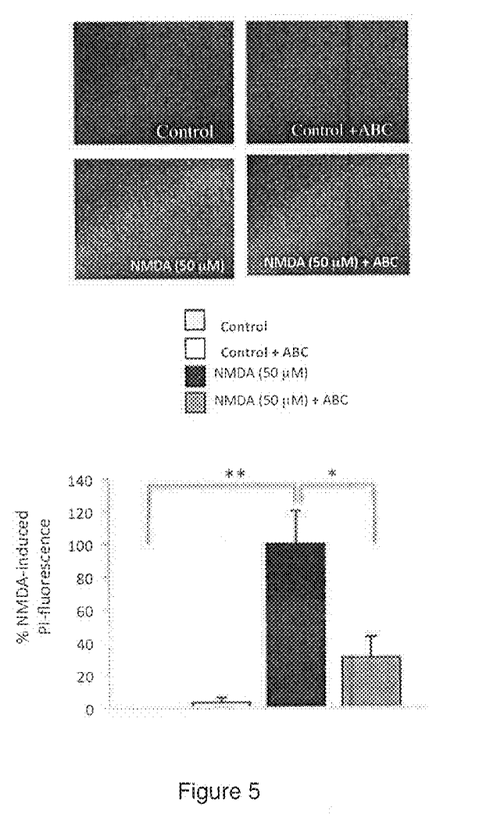
FIG. 5 illustrates the immunofluorescence with propidium iodide of the CA1 area of the hippocampus 24 h after 1 h of treatment with NMDA (50 µM) in the presence or absence of the ABC mixture.

The results of the assay with MTT after 72 h of treatment with zebrafish extract are illustrated in FIG. 3.

After 72 h of treatment, we can conclude that:
  Stages 4, 5 and 6 inhibit the proliferation of hMSCs;
  The effect of the extracts was dose-dependent (for all stages, 10 µg/ml had the more pronounced effect).

Comparison of the results with MTT after 24 and 72 h, assay with MTT after 72 h of treatment with zebrafish.

Comparing the 24 and 72 h, highlights that the early stages (i.e. 1, 2 and 3) and the late stages influence prolif-

TABLE 1

List of protein identified using the nano _LC-ESI-TOF in the zebrafish embryo in the mid-blastula-gastrula phase

| Access | Protein name | Score | Molecular weight | Calculated pI | Sequence coverage |
|---|---|---|---|---|---|
| gi\|166795887 | Precursor of vitellogenin 1 | 1108 | 150308 | 8.68 | 19 |
| gi\|94733730 | Vitellogenin 1 | 1039 | 149825 | 8.74 | 21 |
| gi\|94733733 | New protein similar to vitellogenin 1 (vg1) | 913 | 149828 | 8.92 | 19 |
| gi\|94733734 | New protein similar to vitellogenin 1 (vg1) | 835 | 150550 | 8.83 | 16 |
| gi\|145337918 | Vtg1 protein | 780 | 116965 | 9.07 | 18 |
| gi\|94733731 | New protein similar to vitellogenin 1 (vg1) | 762 | 149911 | 8.84 | 19 |
| gi\|94732723 | New protein simitar to vitellogenin 1 (vg1) | 745 | 147826 | 8.73 | 17 |
| gi\|159155252 * | Protein Zgc: 136383 | 720 | 124413 | 8.78 | 17 |
| gi\|68448530 | Vitellogenin 5 | 559 | 149609 | 8.77 | 13 |
| gi\|92097636 | Zgc: 136383 | 402 | 28924 | 9.33 | 36 |
| gi\|63100501 | Protein Vtg1 | 345 | 36580 | 9.23 | 28 |
| gi\|57864789 | Vitellogenin 7 | 341 | 24490 | 8.37 | 40 |
| gi\|57864783 | Vitellogenin 4 | 334 | 31304 | 9.48 | 27 |
| gi\|113678458 | Precursor of vitellogenin 2 isoform 1 | 323 | 181208 | 8.70 | 11 |
| gi\|125857991 | Protein Zgc: 136383 | 171 | 149328 | 8.93 | 9 |
| gi\|15209312 * | Type 1 procollagen alpha chain 2 | 169 | 147826 | 9.35 | 4 |
| gi\|57864779 | Vitellogenin 2 | 122 | 69906 | 7.84 | 8 |
| gi\|11118642 | Precursor of vitellogenin 3 | 117 | 140477 | 6.92 | 2 |
| gi\|303227889 | Vitellogenin 6 | 73 | 151677 | 8.84 | 4 |
| gi\|13242157 * | Protein ZP2 of the pellucid membrane of the egg | 71 | 48194 | 6.04 | 5 |
| gi\|6644111 * | nucleoside diphosphate kinase-Z1 | 69 | 17397 | 7.77 | 14 |
| gi\|18859071 * | nucleoside diphosphate kinase 3 | 69 | 19558 | 7.68 | 7 |
| gi\|126632622 * | New prot. cont. a galactose binding lectin domain | 67 | 19245 | 9.33 | 13 |
| gi\|66773080 * | Mitochondrial ATP-synthase beta-like subunit | 66 | 55080 | 5.25 | 4 |
| gi\|38541767 * | Ppia protein | 60 | 19745 | 9.30 | 13 |
| gi\|1865782 | Protein HSC70 | 58 | 71473 | 5.18 | 2 |
| gi\|28279108 | Heat shock protein B | 58 | 71382 | 5.32 | 4 |
| gi\|41152402 * | Histone H2B 3 | 49 | 13940 | 10.31 | 11 |
| gi\|41393113 * | Collagen, type 1, alpha 1b precursor | 46 | 137815 | 5.39 | 4 |
| gi\|94732492 * | RAS homologue gene family, member F | 46 | 24035 | 9.00 | 6 |
| gi\|47778620 * | tryptopban hydroxylase D2 | 45 | 55686 | 6.56 | 1 |
| gi\|68448517 * | Glucoprotein of the pellucid zone 3, precursor 2 | 44 | 47365 | 4.92 | 2 |
| gi\|326677766 * | ENVISAGED: RIMS binding protein 2-like | 41 | 138659 | 5.86 | 0 |
| gi\|112419298 | Protein Vtg3 | 40 | 60622 | 6.32 | 2 |
| gi\|54400406 * | Glutaredoxin 3 | 39 | 36541 | 5.18 | 11 |
| gi\|41152400 * | peptidylprolyl isomerase a- like, a-like | 37 | 17763 | 8.26 | 7 |

The ionic score is −10*Log(P), where P is the possibility that the observed is a casual event.
Individual ionic scores >36 indicate identity or extensive homology (p < 0.05).
Individual protein scores are derived from ionic scores as a non-probabilistic basis for ranking protein bits.

eration in a different way, with stages 4, 5 and 6 being the most effective (i.e. less proliferation):

4. Relative Quantitative RT-PCR (Gene Expression)

In order to study the effect of embryonic zebrafish extracts on differentiation, gene expression was analysed after incubation with the extracts. Since the assay with MTT indicated that the more pronounced effect was observed after treatment with the ZF6 extract (a mixture of 5 stages), gene expression was studied after treatment with this extract in concentrations ranging from 0.01-10 µg/ml.

The studied genes are markers for:
stem cell potential (OCT3/4 and KLF4)
cardiogenesis (NKX2.5 and MEF2C)
vasculogenesis (VEGF)
neurogenesis (NEUROG1)
myogenesis (MyoD).

Gene expression was analysed using relative quantitative RT-PCR after 24, 72 hours, and 7 days of treatment. Gene expression was normalised to a domestic gene (HK) (GAPDH) and compared against the untreated cells.

Fundamental Principle.

On the basis of the result of the assay with MTT, ZF6 was used to treat the cells before analysing gene expression.

The following concentrations were used:
10 µg/ml in the 24 and 72 h experiments;
−0.01-0.01 µg/ml in the 7-day experiments.

In the first experiments, low concentrations of ZF6 (0.01, 0.1 µg/ml, 1 µg/ml) were used to study gene expression after 7 days of treatment. An additional concentration (10 µg/ml) was added in the 24 and 72 h experiments.

The following experiments were then carried out:
hMSCs treated with ZF6 at 0.01 and 0.1 µg/ml and RNA extraction after 7 days (n=2);
hMSCs treated with ZF6 at 1 µg/ml and RNA extraction after 7 days (n=1);
hMSCs treated with ZF6 at 10, 1, 0.01 and 0.1 µg/ml and RNA and protein extraction after 24 h (n=1);
hMSCs treated with ZF6 to 10, 1, 0.01 and 0.1 µg/ml and RNA and protein extraction after 72 h (n=1).

Results

The results after 7 days of treatment with ZF6 have highlighted:
Treatment with ZF6 0.01 µg/ml induces a weak negative modulation (change in times<1) of OCT3/4, the expressions of KLF4 VEGF (blue bars) as well as a positive modulation of the expressions of NKX2.5 iMEF2C;
Treatment with ZF6 0.1 µg/ml appears to induce a positive modulation of the expression of OCT3/4, NKX2.5 and MEF2C and a negative modulation of the expression of VEGF, while the expression of KLF4 is similar to the control.

Analysis of gene expression after 24 h of treatment with ZF6 (10 µg/ml).

We can conclude that after 24 h:
Treatment with ZF6 induced a positive modulation of the expression of VEGF and MEF2C;
Treatment with ZF6 induced a negative modulation of the expression of KLF4 and NKX2.5.
The expression of OCT3/4 (marker of stem cell potential) was not affected.

Analysis of Gene Expression after 72 h of Treatment with ZF6 (10 µg/ml).

We can conclude that after 72 h:
Treatment with ZF6 induced a positive modulation of the expression of VEGF and MEF2C;
Treatment with ZF6 induced a negative modulation of the expression of NKX2.5.

The expression of OCT3/4 and KLF4 was not affected.
The expression of NEUROG and MyoD was not detected in the cells treated or in the controls.

In conclusion, it has been demonstrated that the factors (in particular those present in ZF1+ZF2, ZF5 and ZF6) have led to a slowing down of cell proliferation and to an increase in programmed cell death, or apoptosis, while the early stages also highlighted a multiplicative effect. None of the stages and doses tested led to death by necrosis or to toxicity for the cells. The extracts thus proved harmless, and safe.

Example 2

Study of the effects produced by factors collected in 3 different stages of differentiation [A=ZF1+ZF2 (mid-blastula-gastrula+tail bud), B=ZF1+ZF2+ZF5: (mid-blastula-gastrula+tail bud+early pharyngula stage), C=ZF6 (a mixture of mid-blastula-gastrula+tail bud+5-somite+20-somite+early pharyngula stage) in preventing the neurodegeneration of hippocampus cells.

Organotypical hippocampal slices were prepared as previously described (Gardoni et al., 2002) using 7-8-day rats; all pharmacological treatments were carried out in organotypical slices on the 14th day in culture (DIV14).

To test the effect of the zebrafish extract, organotypical slices were exposed to NMDA 50 µM or to NMDA 300 µM in serum free medium, in the presence or absence of the extracts. In some experiments, the slices were incubated for one hour in serum-free medium in the presence or absence of the extracts. For each type of treatment, the neuroprotective activity of both the mixture of the extracts (A+B+C) and the individual extracts (A or B or C), was evaluated.

After one hour, the slices were washed with serum-free medium and then incubated with their medium in the presence or absence of the zebrafish extract for 24 hours.

Fluorescence was used, in combination with the use of propidium iodide (PI) (5 mg/ml) as previously described (Pellegrini-Giampietro et al. 1999), to evaluate the cell damage induced by the different treatments. Quantitative analysis of cell mortality was performed in the CA1 area of the hippocampus using the maximum cell damage obtained by exposing the organotypical slices to treatment with NMDA, as term of comparison.

The images were acquired with a Zeiss Axiovert 200M (10× lens) epifluorescence microscope, and CoolSnap CCD camera. For the quantitative analysis, the images were acquired with the same settings and exposure times. The average intensity of fluorescence was determined after tracing the area corresponding to the CA1 area and the mortality analysed as a function of the fluorescence intensity and of the area expressed as pixel$^2$.

Results.

A first series of experiments was carried out in order to establish the optimal experimental conditions for the evaluation of a possible action of the neuroprotective type of the zebrafish extracts.

For this purpose, we verified that treatment for 1 h with NMDA 50 µM and 300 µM induced a significant mortality in our experimental conditions. Organotypical hippocampal slices (DIV14) were treated for one hour with NMDA 50 µM, or with NMDA 300 µM, so as to have a condition that determines certain mortality, and staining with PI was carried out 24 h thereafter. After fixation, the CA1 was acquired and the mortality analysed as described in the materials and methods. Treatment with NMDA 50 µM determines a 47% increase in mortality (NMDA 50 µM vs CTRL) while NMDA 300 µM determines a 139% increase (NMDA 300 µM vs CTRL).

The neuroprotective properties of the extracts were then evaluated following exposure of the organotypical hippocampal slices to three different toxic stimuli, of different intensity (deprivation serum, NMDA 50 µM, NMDA, 300 µM; 1 h). In a first series of experiments, the possible neuroprotective effect of the mixture of ABC extracts was analysed. The mixture was contemporaneously added (1:100 dilution) to treatment with NMDA or to simple serum deprivation and the analyses were carried out after 24 h.

Figure 6:
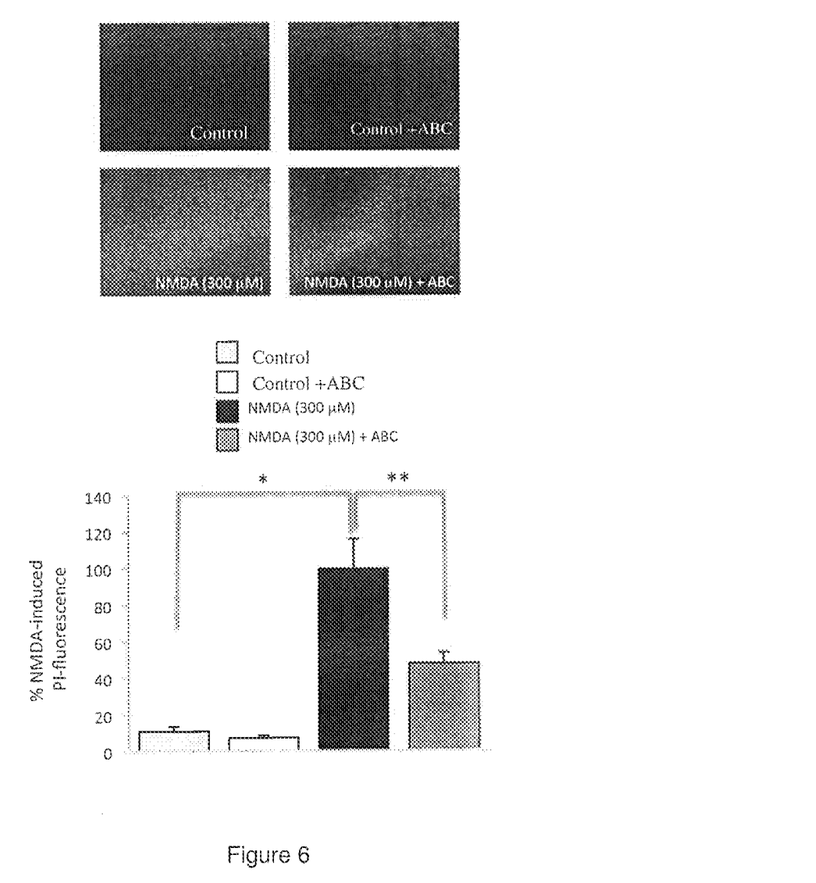
FIG. 6 illustrates the immunofluorescence with propidium iodide of the CA1 area of the hippocampus 24 h after 1 h of treatment with NMDA (300 µM) in the presence or absence of the ABC mixture.

As shown in FIG. 6, treatment with the ABC mixture determines a significant reduction in neuronal mortality ($-31.6\pm6.2\%$, *$p=0.005$) induced by 1 h of serum deprivation.

Figure 7:
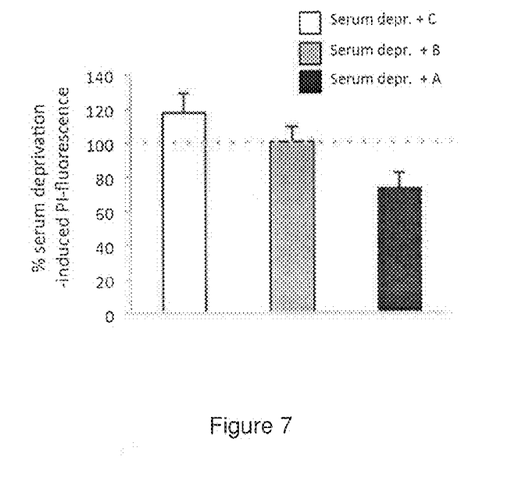
FIG. 7 illustrates the quantisation of the immunofluorescence with propidium iodide of the CA1 area of the hippocampus 24 h after 1 h of serum deprivation in the presence or absence of the individual extracts A, B or C.

Treatment with NMDA (50 µM) caused a significant increase in mortality in the CA1 area (**$p=0.002$, NMDA 50 µM vs CTRL); cotreatment with the ABC mixture determines a significant reduction in the mortality induced by NMDA (50 µM) (FIG. 7; *$p=0.01$, NMDA 50 µM+ABC vs NMDA 50 µM).

In a last series of experiments, the capacity of the ABC mixture to induce neuroprotection even after treatment of hippocampal slices with even higher concentrations of NMDA (300 µM). Even under these experimental conditions, cotreatment with the ABC mixture determines a significant reduction in the mortality induced by NMDA (300 µM) (FIG. 8; *$p=0.0002$, NMDA 300 µM vs control; ** $p=0.009$ NMDA 300 µM+ABC vs NMDA 300 µM).

Figure 8:
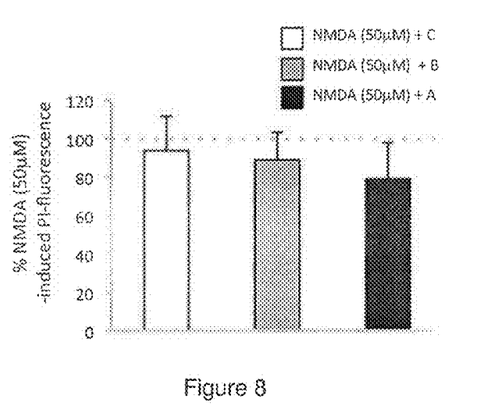
FIG. 8 illustrates the quantisation of the immunofluorescence with propidium iodide of the CA1 area of the hippocampus after 24 h of treatment with NMDA (50 µM; 1 h) in the presence or absence of the individual extracts A, B or C.

The possible neuroprotective properties of the individually administered extracts (A, B or C) was subsequently evaluated. In this case also, the neuronal mortality was evaluated, through the assay with propidium iodide, following exposure of the organotypical hippocampal slices to serum deprivation or to NMDA, in the presence of the various zebrafish extracts. As shown in FIGS. 7 and 8, none of the individual extracts has shown a significant neuroprotective capacity, either following serum deprivation (FIG. 7) or following treatment with NMDA (50 µM; FIG. 8).

DISCUSSION AND CONCLUSIONS

In this study we have assessed the neuroprotective properties of zebrafish extracts, both administered as a mixture of the three extracts, and as individual extracts (A, B, C), following exposure of organotypical hippocampal slices to various types of neurotoxic insults.

The best results in terms of neuroprotection with regard to each type of toxic insult analysed were obtained using the A+B+C mixture. Extract A also showed a certain neuroprotective action, which can be defined at the limit of significance, especially with regard to cell death induced by serum deprivation.

The A+B+C mixture of extracts has, on the other hand, demonstrated a significant neuroprotective activity with regard to the neuronal death induced by 1 h of serum deprivation or induced by treatment with NMDA (both 50 µM and 300 µM). This means that a certain redundancy of information must be used to obtain the best response.

What is claimed is:

1. A composition comprising of a mixture of extracts from a fish embryo in five selected stages of stem cell differentiation, said selected stages consisting of the mid-blastula-gastrula, tail bud, pharyngula, 5-somite and 20-somite stages, wherein the weight percentage of the extract from each of the five stages varies from 5% to 50% in the composition.

2. The composition according to claim 1, wherein said fish is a zebrafish.

3. A method for the treatment of a degenerative diseases of the human body comprising administering a therapeutically effective amount of the composition of claim 1.

4. The method according to claim 3, wherein said degenerative disease is selected from a neurodegenerative or cardiovascular disease.

5. A method for the treatment of cancer comprising administering a therapeutically effective amount of the composition of claim 1.

6. A method for regenerating a human body tissue comprising administering a therapeutically effective amount of the composition according to claim 1.

7. The composition of claim 1, further comprising a physiologically acceptable carrier.

8. The composition according to claim 7 wherein said composition is selected from a pharmaceutical, nutraceutical or a cosmetic composition.

9. A method for treatment of skin comprising applying a cosmetically effective amount of the composition of claim 1.

10. The method of claim 9, comprising treatment of skin wrinkles or skin aging.

* * * * *